United States Patent [19]

Chou

[11] 4,340,609
[45] Jul. 20, 1982

[54] AMIDINOUREA DERIVATIVE VETERINARY COMPOSITIONS FOR SUPPRESSION OF PARASITEMIA

[75] Inventor: Billy J. Chou, Paoli, Pa.

[73] Assignee: William H. Rorer, Inc., Fort Washington, Pa.

[21] Appl. No.: 109,038

[22] Filed: Jan. 2, 1980

[51] Int. Cl.$^3$ .............................................. A61K 31/17
[52] U.S. Cl. ................................... 424/322; 424/246; 424/249; 424/250; 424/251; 424/256; 424/263; 424/267; 424/269; 424/270; 424/272; 424/273 R; 424/273 P; 424/274; 424/303; 424/304; 424/311; 424/317; 424/320; 424/248.54
[58] Field of Search ............... 424/322, 303, 304, 320, 424/317, 311, 285, 263, 246, 248, 249, 250, 251, 256, 267, 269, 270, 272, 273, 273 P, 274; 564/48

[56] References Cited

U.S. PATENT DOCUMENTS

| | | | |
|---|---|---|---|
| 3,539,616 | 11/1970 | Walls | 260/465 |
| 3,984,467 | 10/1976 | Diana | 564/48 |
| 4,163,022 | 7/1979 | Diamond | 564/48 |

OTHER PUBLICATIONS

Curd, F. H. S. et al., "Synthetic Antimalarials, Part XLII, The Preparation of Guanylureas and Biurets corresponding to "Paludrine" and related Biguanides", J. Chem. Soc., p. 1732 (1949).
Skowronska-Serafin, B. and Urbanski, T., "Preparation of Derivatives of Amidineurea and their Reactions", Tetrahedron, vol. 10, pp. 12–24 (1960).
Goodford, Walls et al., "Predictions of the antimalarial activity of arylamidinoureas", Br. J. Pharmac., vol. 48, pp. 650–654 (1973).
Douglas et al., Arzneimittel Forschung (Drug Research), 28(II), pp. 1433–1480 (1978).

*Primary Examiner*—Sam Rosen
*Attorney, Agent, or Firm*—James A. Nicholson; Alexis Barron; Martin F. Savitzky

[57] ABSTRACT

Therapeutic compositions containing an amidinourea are used in the treatment of animals infested with blood residing parasites, particularly parasitic protozoal infestations of the blood and blood-forming organs.

17 Claims, No Drawings

AMIDINOUREA DERIVATIVE VETERINARY COMPOSITIONS FOR SUPPRESSION OF PARASITEMIA

BACKGROUND

The control of diseases caused by blood residing parasites is of major importance in veterinary medicine. Parasitic infestations of the blood and blood-forming organs in both domestic animals and in wild animals results in substantial direct economic loss each year owing to death and debilitation. Further economic losses are incurred by the need to separate diseased animals and the necessary and attendant restrictions on herd movements imposed by quarantine laws. The most significant losses from blood residing parasites are caused by parasitic worms, particularly filaria and by parasitic protozoa especially plasmodiam and babesia.

Among the filaria diseases, canine heart worm caused by *Dirofilaria immitis* is prevalent along the East and Gulf coasts of the United States where as many as 50% of dogs may be affected. Filariasis or heart worm disease appears to be a growing problem throughout the United States and other countries and is not confined to dogs, but may be found in other animal species such as cats, seal, brown bear, wolverine, coyotes and rarely in humans. Presently available treatments and therapeutic agents are limited and are not entirely effective. The drugs currently in use include Levamisole (Tetramisole hydrochloride) and Arsenamide (Thiacetarsamide Sodium).

Animal diseases caused by blood residing parasitic protozoa are comon among horses, cattle, goats and sheep and include equine babesiasis, bovine babesiasis, anaplasmosis and piroplasmosis. These diseases are characterized by the presence of parasitic protozoa in the blood stream of the infected animal where the protozoa attack the red blood cells, causing anemia.

Piroplasmosis in horses, known as Equine Piroplasmosis, equine babesiasis, or equine malaria, is an acute, subacute and/or chronic hemoprotozoan infectious disease of solipeds, caused by *Babesis caballi*, or *B. equi*, and characterized in clinical cases by intermittent fever, weakness, constipation, anemia, icterus, and edema. This disease is reported to be world-wide. The infecting protozoa may be transmitted by various species of ticks, by parenteral injection of blood or organ emulsion, or by intrauterine transmission. Horses, mules, donkeys, and zebra are especially susceptible to this disease. Peracute cases are fatal, while less severe acute and subacute cases may recover. Currently available treatments are not generally effective, and owing to difficulty in detecting the disease, treatment is frequently started too late. Commonly used therapeutic agents are birenil, acaprin, and acriflavin. However, these are reported only to reduce the number of parasites.

Piroplasmosis and babesiasis in cattle, also known as Texas fever, is an infectious disease of bovines caused by *Babesia digeminum* which affects erythrocytes and is primarily propagated by ticks. It is characterized by an acute condition with or without hemoglobinuria and a chronic state of latent infection. Animals infected with Texas fever in a very acute condition have little chance of surviving without treatment. Common therapeutic agents include trypan blue, acaprin, phenadrine, and berenil.

Anaplasmosis of cattle, sheep and goats is caused by infection with Anaplasma spp. The causative agent in sheep and goats is *A. ovis*. The infectious disease of cattle is caused by progressive anemia due to erythrocyte destruction. The disease is widely distributed in the warmer climates of the United States and transmitted by blood-sucking insects as well as by mechanical means. Bovine is the parasitic natural host, while buffalo, zebra, deer and other wild ruminants act as natural reservoirs. The prognosis for this disease is 50 to 70% recovery, and recovered animals continue to be a hazard due to their carrier condition. Treatment for this disease may be effected by utilizing antibiotics, such as terramycin, aureomycin or tetracyclines, if given in the early stages of infection. Carrier eradication may be effected with aurofac in cattle feed for a prolonged period of time. Anaplasmosis is now present in 40 of the 50 states of the United States and is reported to cost this country $35,000,000 annually.

Parasitic protozoal infestations are difficult diseases to eradicate due to the fact that there are a large number of insects capable of being carriers of these diseases. Furthermore, the armament of drugs utilized to halt the proliferation of these parasites may lose their efficacy due to the evolution of drug resistant protozoic strains.

Anti-malarial related research indicates that there are basically two known mechanisms responsible for chemotherapeutic anti-malarial action as well as related protozoal diseases. The first mechanism responsible for the action of the oldest known antimalarial agent, quinine, is that of non-specific DNA binding or intercalation. The second proposed mechanism is specific to protozoic diseases. Protozoa incorporate para-aminobenzoic acid into folic acid, a process which does not occur in mammals in their metabolic machinery and require a supply of para-amino benzoic acid in order to synthesize their own folinic acid. Folic acid enzyme antagonists therefore have been found to exhibit anti-protozoal activity. Interference with the enzymatic machinery of this synthetic pathway may be responsible for this selective anti-protozoal action. Drugs known to act in this fashion include chloroguanide, cycloguanial pamoate, pyrimethamine and its derivatives, as well as sulphamides and sulphones.

Among the folinic acid antagonists, the biguanide members may be, in some cases, transformed in the host body to form active triazine metabolites. However, the triazine metabolite of chloroquanide has little or no usefulness in the therapy of humans and monkeys due to its rapid excretion from the body. Moreover, this latter class of compounds, that is, the folinic acid inhibitors, are most susceptible to a loss of efficacy due to the appearance of therapeutically resistant strains of protozoa. In fact, *P. berghei* is known as a pyrimethamine resistant protozoal strain. Structural changes in the triazine rings of the presumably active form of these anti-protozoal drugs, as well as its method of administration, may modify the activity unpredictably as well as alter the rate of excretion of the drug from the host body. For example, while in malaria cases, chloroguanide is rapidly excreted from the body when in its triazine form and has little or no usefulness, chloroguanide triazine pamoate, when tested with *P. berghei* infected mice, has good and lasting effects with a single muscular injection and is not excreted rapidly from the host body. Owing to such unpredictability and the limited drugs available for treatment of animal diseases caused by blood-residing parasites, there is need for effective drugs for use in the treatment of these animal diseases.

SUMMARY OF THE INVENTION

It has now been found that amidinoureas are effective in the treatment of diseases caused by blood-residing organisms, especially in diseases and anemia caused by blood-residing protozoa, particularly anamplasmosis and babesiasis, and is useful in the treatment of diseases caused by blood-residing helminths, particularly, heart worm.

This invention relates to the use of amidinoureas in the treatment of animal diseases caused by blood-residing parasites and to novel veterinarian compositions containing an effective amount of an amidinourea and administration of such compositions to exposed or infected animals for prevention and treatment of the disease, and relief of symptoms, particularly for the treatment of protozoic and helminthic infestations of domestic and wild animals such as equine, bovine, canine and feline species. In particular, the diseases to be treated with these compositions are the various strains of babesiasis, anaplasmosis and heart worm.

Since these compounds have been found to be readily absorbed through the mammalian intestinal wall, an effective amount of amidinourea can be administered prophylactically or to suppress or control the disease in the form of veterinary compositions formulated as tablets, capsules or liquids suitable for oral administration. Alternatively, the amidinourea may be formulated as a dietary supplement suitable for incorporating into the solid or liquid dietary intake of the animals. The amidinourea can be intravenously or intramuscularly injected and may be combined with other therapeutic agents such as sulphonamides, sulphones, antibiotics or with other suitable excipients.

OBJECTS

It is an object of this invention to provide an effective treatment for animals infected with blood-residing parasitemic infestations.

In particular, it is an object of this invention to provide an effective treatment for conditions brought about by blood-residing helminths, for example, canine heart worm, *Dirofilaria immitis* and related filarioidea.

It is a further object of the invention to provide an effective treatment for animals suffering from diseases caused by blood-residing protozoal infestations, and in particular, protozoal infestations of cattle, horses, sheep and goats.

It is still a further object of this invention to provide an amidinourea composition for the suppression of parasitemia caused by strains of blood-residing protozoa that have developed resistance to treatment with folic acid antagonists.

It is still a further object of this invention to provide an effective treatment for animal anaplasmosis, piraplasmosis, babesiasis, and dirofilariasis.

It is still a further object of this invention to provide compositions of amidinoureas, effective against protozoal infestations, in combination with sulphur compounds, antibiotics and/or other therapeutic agents.

It is still a further object of this invention to provide a therapeutic composition for suppression of parasitemia comprising an amidinourea which, when administered to animals infested with blood-residing parasites, has a long-lasting effect and is not quickly excreted from the host body.

The therapeutic compositions of this invention effective against parasitic infestations and desirable for use in livestock, combine specificity of action, moderate duration of host retention, and a high therapeutic index (therapeutic index is described as the ratio of the 50% suppressant dose to the 50% lethal dose). Standardized screening techniques for the identification of active compositions indicate that amidinoureas possess surprising therapeutic activity with respect to parasitic blood-related disease. The theory of action of these drugs, as described above, is given by way of illustration only and is not to be construed as limiting the invention in any way.

DETAILED DESCRIPTION OF THE INVENTION

A preferred embodiment of this invention is the treatment of domestic animals affected with helminthic blood-residing diseases such as *dirofilaria immitis*, with a therapeutic composition containing an effective amount of an amidinourea of Formula I.

Protozoic infestations responsible for equine piraplasmosis and bovine anaplasmosis cause substantial economic loss in the United States. Another preferred embodiment of this invention is the administration of a composition containing an amidinourea to domestic animals such as cattle, horses, sheep and goats for treatment of bovine anaplasmosis, equine piroplasmosis, texas fever and related diseases caused by blood-residing parasitic protozoa.

The amidinoureas which are suitable for use in the method of this invention and which comprise the principal active ingredient in the veterinary compositions of this invention are the compounds of the formula:

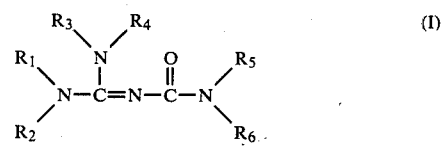

wherein one of $R_1$ or $R_5$ is phenyl, phenyl in which one or more of the hydrogens is substituted by halo, lower alkyl, halo lower alkyl, nitro, amino, acylamino, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ or $R_5$ is hydrogen, lower alkyl, lower alkoxy, lower alkenyl, cyclo lower alkenyl, cyclo lower alkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen, or sulfur; and when $R_5$ is phenyl, phenyl substituted as above, aralkyl, pyridyl, or pyridyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

As employed above and throughout the disclosure, the following terms, unless otherwise indicated, shall be understood to have the following meanings:

"alkyl" means a saturated aliphatic hydrocarbon which may be either straight or branched chain, lower alkyl being preferred; also included are the cycloalkyl groups such as cyclohexyl, cyclopropyl, etc., and the cycloalkyl lower alkyl groups such as cyclopropylmethyl and the like.

"lower alkyl" means an alkyl group as above having about 1 to about 6 carbon atoms. Suitable lower alkyl groups are methyl, ethyl, propyl, isopropyl, butyl, sec-butyl, tert-butyl, pentyl and isopentyl.

"cycloalkyl" means an aliphatic monocyclic saturated carbocyclic group having about 3 to about 6 carbon atoms, preferably cyclopropyl, cyclopentyl and cyclohexyl.

"alkenyl" means an unsaturated aliphatic hydrocarbon which contains one or more double bonds and which may be straight or branched chain with lower alkenyl, i.e. alkenyl of about 2 to about 6 carbons being preferred.

"lower alkenyl" means alkenyl of about 2 to about 6 carbon atoms such as ethylene, propylene, butylene, isobutylene, etc.

"alkynyl" means an unsaturated aliphatic hydrocarbon containing one or more triple bonds with lower alkynyl, i.e. alkynyl of about 2 to about 6 carbons being preferred.

"lower alkynyl" means alkynyl of about 2 to about 6 carbon atoms such as propargyl, butynyl, pentynyl, etc.

"aryl" means phenyl and substituted phenyl.

"substituted phenyl" means a phenyl group in which one or more of the hydrogens has been replaced by the same or different substituents including halo, lower alkyl, halo lower alkyl, nitro, amino, acylamino, hydroxy, lower alkoxy, aryl-lower alkoxy, acyloxy, cyano, halo lower alkoxy or lower alkyl sulfonyl.

"aralkyl" means an alkyl (preferably a lower alkyl) in which one or more hydrogens is substituted by an aryl moiety (preferably phenyl or substituted phenyl), e.g. benzyl, phenethyl, etc.

"5 and 6 membered heterocyclic group" means a 5 or 6 membered ring having about 1 to about 3 hetero atoms which may be nitrogen, oxygen or sulfur including pyridyl, 2-pyridyl or 3-pyridyl; pyrimidyl, pyrazolyl, imidazoyl, furyl, thienyl, oxazonyl, thiazolyl, piperidyl, piperazenyl, morpholinyl, thiomorpholinyl, etc., with the pyridyl groups being preferred.

"substituted pyridyl" means a pyridyl in which one or more of the hydrogens on the ring carbons have been replaced by substituents as given above with respect to substituted phenyl. The pyridyl substituents may be either 2-, 3-, or 4-pyridyls; preferred substituted pyridyls are those having substituents on the carbon or carbon atoms vicinal to the carbon attached to the amidino or urea nitrogen.

The terms "halo" and "halogen" include all four halogens; namely, fluorine, chlorine, bromine and iodine.

Halo alkyl and halophenyl include alkyl or phenyl groups having more than one halo substituent which may be the same or different such as trifluoromethyl, 1-chloro-2-bromo ethyl, chlorophenyl, 2-chloro-6-bromophenyl, etc.

The term "acyl" means an organic acid radical, preferably a lower alkanoyl or aroyl, e.g. acetyl, propionyl, benzoyl, benzenesulfonyl, etc.

The term "acyloxy" is intended to mean an organic acid radical such as acetoxy, propionoxy, benzoyloxy, and the like.

The term "acylamino" is intended to mean an organic amido group of the RCONH type where R is an organic radical preferably lower alkyl or aryl lower alkyl.

The term "lower alkanoyl" is intended to include the acid radical of a lower alkanoic acid such as acetyl, propionyl and the like.

It should be understood that whereas the structure of the starting materials are shown here in a particular configuration for purposes of illustration, the compounds may exist in various enolized or tautomeric forms, particularly where one of $R_3$ and $R_4$ is hydrogen, shown for example, by the following formula:

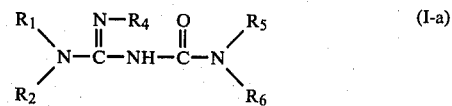

(I-a)

Certain of the compounds can also be obtained as hydrates or in different polymorphic forms. The structures used herein to designate novel compounds are intended to include the compound shown along with its alternative or transient states.

Among the amidinoureas of Formula I, a particularly preferred group of amidinoureas suitable for use in the composition and method of this invention are those in which the $R_5$ or $R_1$ substituent is a phenyl or substituted phenyl and particularly, a phenyl having substituents in the 2 and 6 positions (i.e. ortho to the carbon attached to the urea nitrogen). Such preferred compounds can be represented by the formulae:

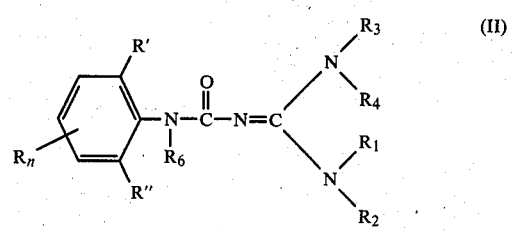

(II)

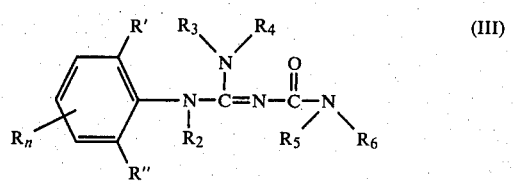

(III)

wherein $R_1$, $R_2$, $R_3$, $R_4$ and $R_6$ all have the same meanings as above, and $R_n$ represents one, two or three substituents in any one or more the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl; $R'$ and $R''$ are hydrogen, halo, lower alkyl, halo lower alkyl, nitro, lower alkoxy, hydroxy, aryl lower alkoxy, acyloxy, halo lower alkoxy, or lower alkyl sulfonyl; and $R_n$ represents one, two or three substituents in any one or more of the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl.

Particularly preferred compounds of Formula I-a are those wherein the phenyl substituents are lower alkyl, lower alkoxy, or halo; and one of $R_1$, $R_2$, $R_3$, and $R_4$ is hydrogen, and the others are lower alkyl, halo lower alkyl or lower alkoxy lower alkyl. The preferred alkyl substituents are methyl, ethyl, propyl, and isopropyl. The preferred halo substituents are chlorine and bromine. The preferred halo lower alkyl substituents are chloromethyl and trifluoromethyl.

A most preferred group of amidinoureas suitable for use in the practice of this invention are the compounds of the formula:

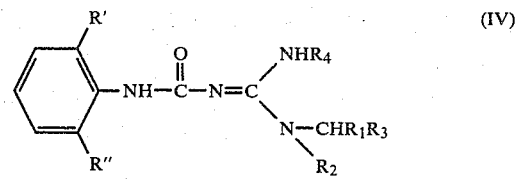

(IV)

wherein $R_1$ and $R_2$, $R_3$, $R_4$ are each hydrogen, lower alkyl, lower alkoxy or hydroxy; and $R'$ and $R''$ are each hydrogen, halo or lower alkyl.
and the formula:

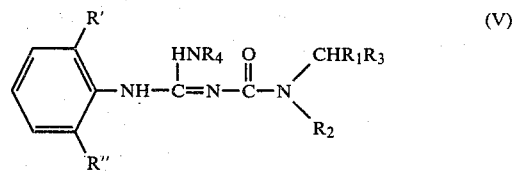

(V)

The compounds of Formula I, I-a, II or III can be used in the practice of this invention in the form of the base or as salts prepared by reacting the compounds of Formula I with pharmaceutically acceptable acids. Suitable acid addition salts are, for example, the salts derived from the following organic and inorganic acids: hydrochloric acid, nitric acid, sulfuric acid, phosphorous acid, orthophosphoric acid, etc.; aliphatic mono- and di-carboxylic acids such as acetic acid, propionic acid, succinic acid, formic acid, caprylic acid, maleic acid, oxalic acid, malonic acid, etc.; phenyl-substituted alkanoic acids, hydroxy alkanoic acids, aromatic carboxylic acids, and aliphatic and aromatic sulfonic acids such as methylbenzoic acid, phthalic acid, benzenesulfonic acid, phenylpropionate, tartaric acid, citric acid, lactic acid, glycollic acid, phenylacetic acid, phenylbutyric acid, methanesulfonic acid, etc.

Suitable amidinoureas for use in the veterinary treatment method of this invention are those disclosed in U.S. Pat. Nos. 4,115,647; 4,088,785; 4,025,652; 4,115,564; 4,060,635; and 4,058,557 and in co-pending application Ser. No. 671,762, now U.S. Pat. No. 4,147,805, the disclosures of which are incorporated herein by reference.

The amidinoureas employed as the principal active ingredient in the composition and method are prepared by methods known in the art.

Exemplary compounds prepared in accordance with such teachings for utilization in this invention are named below wherein the urea nitrogens are designated as positions 1 and 3 respectively:
1-(2,6-dimethylphenyl)-3-methylamidinourea
0-chlorophenylamidinourea
(2,3-dichlorophenylamidino)urea
(2,4-dichlorophenylamidino)urea
(2,5-dichlorophenylamidino)urea
(3,4-dichlorophenylamidino)urea
(3,5-dichlorophenylamidino)urea
(2,6-dichlorophenylamidino)urea
m-chlorophenylamidinourea
p-chlorophenylamidinourea
3,4-diflourophenylamidinourea
m-bromophenylamidinourea
p-bromophenylamidinourea
3,4-dibromophenylamidinourea
3-chloro-4-bromophenylamidinourea
3-bromo-4-chlorophenylamidinourea
3-chloro-4-fluorophenylamidinourea
3-bromo-4-fluorophenylamidinourea
3-fluoro-4-chlorophenylamidinourea
2,6-dimethylphenylamidinourea
2,6-diethylphenylamidinourea
2-methyl-6-ethylphenylamidinourea
2-methyl-6-methoxyphenylamidinourea
2-methyl-6-ethoxyphenylamidinourea
2-ethyl-6-ethoxyphenylamidinourea
3,4-dihydroxyphenylamidinourea
3,4-dimethoxyphenylamidinourea
3,4,5-trimethoxyphenylamidinourea
3,4,5-trihydroxyphenylamidinourea
1-(2,6-dimethylphenylamidino-3,3-(N-methyl-3'-azapentamethylene)urea
1-(2,6-dimethylphenylamidino)-3,3-(N-methyl-3'-azahexamethylene)urea
1-(2,6-dimethylphenylamidino)-3,3-(3'-oxapentamethylene)urea
1-(2,6-dimethylphenylamidino)-3,3-(2'-thiatetramethylene)urea
1-(2,6-dimethylphenylamidino)-3,3-tetramethyleneurea
1-(p-fluorophenylamidino)-3,3-($\alpha,\alpha'$-dimethylpentamethylene)urea
1-(p-chlorophenylamidino)-3,3-(pentamethylene)urea
1-(2,6-dimethylphenylamidino)-3,3-($\alpha,\alpha'$-dimethylpentamethylene)urea
1-(2,6-dimethylphenylamidino)-3,3-pentamethyleneurea
1-(2,6-dimethylphenylamidino)-3,3-($\alpha$-methylpentamethylene)urea
1-(N-methylamidino)-3-(2,6-dimethylphenyl)urea
1-(N-methylamidino)-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methoxyphenyl)urea
1-amidino-3-(2,6-dimethylphenyl)urea
1-amidino-3-(2-methyl-6-ethylphenyl)urea
1-amidino-3-(2-ethyl-6-bromophenyl)urea
1-amidino-3-(2,-ethyl-6-chlorophenyl)urea 1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methylphenyl)urea
1-amidino-3-(2,6-dimethylphenyl)urea
1-amidino-3-(2-methyl-6-ethylphenyl)urea
1-amidino-3-(2-ethyl-6-bromophenyl)urea
1-amidino-3-(2-ethyl-6-chlorophenyl)urea
1-amidino-3-(2-ethyl-6-methoxyphenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-(2,6-dichlorophenylamidino)-3-n-propylurea
1-(2,6-dimethylphenyl)-3-(isopropylamidino)urea
1-(4-bromo-2-chloro-6-methylphenyl)-3-methylamidino urea
1-(2-bromo-6-methylphenyl)-3-methylamidino urea
1-(2,6-dimethylphenyl)-3-(N-methyl-N'-propylamidino)urea The amidinoureas of Formulae I–V and their pharmaceutically acceptable salts are useful as veterinary medicines. In particular, these compounds are useful in preventing and treating malaria-type diseases and parasitic infestations. Parasitic infestations may be suppressed, or in other words, prevented, controlled or eradicated by administering an effective amount of a compound of Formulae I–V as a food additive, an intraperitoneal injection, an intravenous injection, or an intramuscular injection. The drug may be utilized in the form of a tablet, pill, or any other method known in the art. These compounds may also be utilized in conjunction with antibiotics such as tetracycline, aureomycin, etc., or with other therapeutic agents such as sulphonamides, sulphones, etc. Compounds of Formulae I–V and, in particular, specific compounds identified above, when formulated into therapeutic dosage forms provide a beneficial means for the treatment of animals suffering from diseases caused by blood-residing parasites. The activity and recommended dosage amounts are shown by the following tests.

TEST RESULTS

Methodology

Five representative amidinoureas were tested in mice infected with *plasmodium berghei*. The five compounds tested are the following:

Compound A—1-(2,6-dichlorophenylamidino)-3-n-propylurea
Compound B—1-(2-bromo-6-methylphenyl)-3-methylamidino)urea hydrochloride
Compound C—1-(4-bromo-2-chloro-6-methylphenyl)-3-methylamidinourea hydrochloride
Compound D—1-(2,6-dimethylphenyl)-3-N-methyl-N'-propylamidino)urea hydrochloride
Compound E—1-(2,6-dimethylphenyl)-3-(isopropylamidino)urea hydrochloride Groups of 10 mice each were used in seven doses totaling 70 mice per compound. The protozoal infection was induced by intraperitoneal injection of 5,000,000 parasitized blood cells from a donor. The compound was administered subcutaneously in doses ranging from 0.15 to 10 mg. per kg., suspended on 0.5% methacel solution (doses expressed as base). The compound was repeatedly injected on the day of inoculation (day 1), day 2 and day 3. Blood smears were performed on days 4, 5, 6 and 10. The results are summarized in Tables 1 and 2. From this data it may be concluded that:

(a) All five compounds suppressed infection of *plasmodium berghei*. Mice treated with 10 mg. per kg. daily for three days did not show parasitemia and survived for at least three weeks. Untreated control but infected mice developed fulminating parasitemia of as high as 35% on day 10 and deaths occurred from day 12 to 14.

(b) All five compounds suppressed parasitemia in lower doses, although death still occurred after two weeks time.

(c) The 50% suppressant dose ($SED_{50}$) on day 5 ranged from 1.12 to 1.91 mg. per kg. for the five compounds. It should be noted that on day 10, the $SED_{50}$ ranged from 1.58 to 5.63 mg. per kg. There is a difference in duration of action of the five compounds. Compound A had the lowest $SED_{50}$ on day 10 and the longest duration of action. The order of decreasing $SED_{50}$ or shorter duration of suppression for the remaining four compounds is:

Compound B
Compound C
Compound D
Compound E (d) The factor of change from the lowest $SED_{50}$ to the highest $SED_{50}$ for each compound, measured from day 4 to day 10, is another way of representing the longest duration of action of each compound. The following chart arranges these compounds in order of increasing factor of change as follows:

| COMPOUND | HIGHEST $SED_{50}$ ÷ LOWEST $SED_{50}$ | FACTOR |
|---|---|---|
| B | 1.87 ÷ 1.66 | 1.12 |
| A | 1.58 ÷ 0.71 | 2.23 |
| C | 3.99 ÷ 1.12 | 3.56 |
| D | 4.47 ÷ 0.90 | 4.97 |
| E | 5.63 ÷ 0.90 | 6.26 |

TABLE 1

| Control | Dose mg/kg | Mean of parasitemia in each group of 10 mice | | | | | | | | | | |
|---|---|---|---|---|---|---|---|---|---|---|---|---|
| | | Mean % Parsitemia | | | | Mean % Suppression | | | | % died | | |
| | | 4th day | 5th day | 6th day | 10th day | 4th day | 5th day | 6th day | 10th day | 12th day | 13th day | 14th day |
| | None | 5.25 | 7.30 | 9.30 | 35.50 | 0 | 0 | 0 | 0 | 30 | 70 | 100 |
| COMPOUND C | .15 | 5.00 | 7.20 | 9.20 | 35.40 | 4.8 | 1.4 | 1.1 | 0.3 | 20 | 40 | 80 |
| | .20 | 5.00 | 6.25 | 9.10 | 35.10 | 4.8 | 14.4 | 2.2 | 1.1 | 40 | 60 | 60 |
| | .30 | 4.75 | 6.00 | 8.30 | 33.40 | 9.5 | 17.8 | 10.8 | 5.9 | 20 | 40 | 80 |
| | .50 | 4.75 | 5.20 | 7.00 | 31.40 | 9.5 | 28.8 | 24.7 | 11.5 | 0 | 20 | 80 |
| | 1.0 | 2.75 | 3.60 | 5.20 | 28.30 | 47.6 | 50.7 | 44.1 | 20.3 | 20 | 60 | 60 |
| | 2.0 | 1.50 | 1.90 | 4.10 | 24.28 | 71.4 | 74.0 | 56.0 | 31.6 | 20 | 20 | 40 |
| | 10.0 | 0 | 0 | 0 | 0 | 100.0 | 100.0 | 100.0 | 100.0 | 0 | 0 | 0 |
| COMPOUND D | .15 | 5.00 | 7.40 | 9.20 | 34.0 | 4.8 | 0 | 1.1 | 4.2 | 0 | 20 | 80 |
| | .20 | 4.50 | 7.30 | 9.10 | 30.8 | 14.3 | 0 | 2.2 | 13.2 | 40 | 60 | 100 |
| | .30 | 4.50 | 7.20 | 8.20 | 26.5 | 14.3 | 1.4 | 11.8 | 25.4 | 0 | 0 | 60 |
| | .50 | 3.50 | 7.10 | 7.30 | 24.3 | 33.3 | 2.7 | 21.5 | 31.5 | 20 | 40 | 80 |
| | 1.0 | 2.25 | 6.50 | 6.70 | 22.4 | 57.1 | 11.0 | 28.0 | 36.9 | 20 | 20 | 40 |
| | 2.0 | 1.75 | 3.30 | 4.80 | 20.5 | 66.6 | 54.8 | 48.4 | 42.3 | 20 | 20 | 20 |
| | 10.0 | 0.25 | 0 | 0 | 0 | 96.2 | 100.0 | 100.0 | 100.0 | 0 | 0 | 0 |
| COMPOUND A | 0.15 | 5.00 | 6.90 | 8.10 | 33.02 | 4.8 | 5.5 | 12.9 | 7.0 | 40 | 60 | 80 |
| | .20 | 4.00 | 6.80 | 7.50 | 30.1 | 23.8 | 6.8 | 19.4 | 15.2 | 0 | 20 | 20 |
| | .30 | 3.25 | 6.30 | 7.20 | 28.5 | 38.1 | 13.7 | 22.6 | 19.7 | 0 | 20 | 20 |
| | .50 | 2.75 | 5.00 | 5.40 | 24.8 | 47.6 | 31.5 | 41.9 | 30.1 | 0 | 0 | 40 |
| | 1.0 | 2.50 | 4.20 | 4.60 | 20.4 | 52.3 | 42.5 | 50.5 | 42.5 | 0 | 20 | 40 |
| | 2.0 | 2.25 | 3.00 | 3.80 | 16.5 | 57.1 | 59.0 | 59.1 | 53.5 | 0 | 0 | 20 |
| | 10.0 | 0 | 0 | 0 | 0 | 100.0 | 100.0 | 100.0 | 100.0 | 0 | 0 | 0 |
| COMPOUND B | .15 | 5.00 | 7.00 | 7.80 | 34.1 | 4.8 | 4.1 | 16.1 | 3.9 | 20 | 20 | 20 |
| | .20 | 5.00 | 6.90 | 7.40 | 30.2 | 4.8 | 5.5 | 20.4 | 14.9 | 0 | 20 | 40 |
| | .30 | 4.00 | 6.60 | 6.90 | 29.1 | 23.8 | 9.6 | 25.8 | 18.0 | 0 | 0 | 40 |
| | .50 | 4.00 | 5.10 | 5.80 | 26.7 | 23.8 | 30.1 | 37.6 | 24.8 | 20 | 40 | 60 |
| | 1.0 | 3.75 | 4.30 | 5.10 | 23.2 | 28.6 | 41.1 | 45.2 | 34.6 | 0 | 20 | 20 |
| | 2.0 | 2.50 | 3.40 | 4.50 | 19.8 | 52.3 | 53.2 | 51.6 | 44.2 | 0 | 0 | 20 |
| | 10.0 | 0.25 | 0.50 | 0.05 | 0 | 96.2 | 94.0 | 99.6 | 100.0 | 0 | 0 | 0 |
| COMPOUND E | .20 | 5.25 | 7.00 | 8.70 | 33.9 | 0 | 4.1 | 6.5 | 4.5 | 0 | 60 | 60 |
| | .50 | 2.50 | 6.90 | 7.40 | 31.3 | 52.3 | 5.5 | 20.4 | 11.8 | 0 | 20 | 60 |
| | 2.0 | 1.75 | 3.50 | 4.10 | 27.7 | 66.7 | 52.1 | 55.9 | 22.0 | 0 | 20 | 40 |
| | 10.0 | 0 | 0 | 0 | 0 | 100.0 | 100.0 | 100.0 | 100.0 | 0 | 0 | 0 |

On the 4th, 5th, and 6th day, three mice from each group were examined.

TABLE 2

Calculation of Suppressant Effective Dose$_{50}$ based on levels of parasitemia

| | SED$_{50}$(mg/kg) | | | | |
|---|---|---|---|---|---|
| | 4th day | 5th day | 6th day | 10th day | LD$_{50}$ in Mice (mg/kg) |
| COMPOUND C | 1.12 | 1.12 | 1.39 | 3.99 | |
| COMPOUND D | 0.90 | 1.91 | 2.09 | 4.47 | 222 < LD$_{50}$ < 366 |
| COMPOUND A | 0.71 | 1.20 | 1.05 | 1.58 | LD$_{50}$ > 600 |
| COMPOUND B | 1.87 | 1.87 | 1.66 | 1.87 | 82 < LD$_{50}$ < 135 |
| COMPOUND E | 0.9 | 1.52 | 1.52 | 5.63 | 82 < LD$_{50}$ < 135 |

SUMMARY

These results demonstrate the effectiveness of the amidinoureas in suppressing parasitemia. In particular, these results indicate the effectiveness of the amidinoureas with respect to a resistant strain of infective protozoa, *plasmodium berghei*.

The compositions of the present invention can be prepared in forms suitable for administration by compounding an effective single dose amount of a compound of Formula I above, with known ingredients generally employed in the preparation of therapeutic veterinary compositions provided as tablets, capsules, lozenges, chewable lozenges, pills, powders, granules, suspensions, oil and water, or water and oil emulsions or similar forms which can be taken orally. The treatment can be accomplished by incorporating an effective amount of a compound of Formula I in the animal diet with feed supplement or dissolved in the animal's fluid intake.

The compounds are readily absorbed into the blood stream from the stomach and intestines when taken orally, the preferred method of treatment may be to give the drug orally which is also the safest and most practical route of administration. Optional modes can be used where, for example, the animal is not eating or cannot swallow or has difficulty in swallowing, other methods of administration which permit the drug to be absorbed in the gastrointestinal tract or which deliver a solution of the drug directly to the blood stream can be employed.

The method of administration may also vary depending on the purpose of administration. For example, use as a prophylaxis or preventive treatment, a pre-immunity suppressant or as treatment of infected animals can require different methods of treatment and dosage forms easily formulated by those skilled in the art.

The dosage regimens in carrying out the methods utilizing the amidinourea compositions of this invention for suppression of parasitemia, including treatment of heart worm, are those which insure maximum therapeutic response. The average effective dose is between about 0.1 to about 15 mg. per kg. of body weight with about 1.0 to about 10 mg/kg being preferred.

Compositions intended for oral use may be prepared according to methods known generally in the art, such compositions may contain one or more agents selected from the group consisting of sweetening agents, flavoring agents, coloring agents, and preserving agents, in order to provide a pharmaceutically elegant and palatable preparation. Orally, it may be administered in tablets, lozenges, aqueous or oily suspensions, dispersible powders or granules, emulsions, hard or soft capsules, or syrups or elixers, which contain the active amidinourea ingredient in admixture with non-toxic pharmaceutically acceptable excipients. Excipients which may be, for example, interdilutants such as calcium carbonate, sodium carbonate, lactose, calcium phosphate, or sodium phosphate; granulating disintegrating agents, for example, maize, starch, or algenic acid; binding agents, for example, starch, gelatin, or acacia; and lubricating agents, for example, magnesium stearate, stearic acid, or talc. Tablets may be uncoated or they may be coated by known techniques to make them more effective, for example, to delay disintegration or absorption, or to make them more palatable, or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid parafin or olive oil.

Aqueous solutions containing the active amidinourea form a further embodiment of this invention. Excipients suitable for aqueous suspensions may be employed, if desired. These excipients are suspending agents, for example, sodium carboxymethyl-cellulose, methyl-cellulose, hydroxypropylmethylcellulose, sodium alginate, polyvinylpryyolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethylenoeoxy-cetanol; or condensation products of ethylene oxide with partial esters derived from fatty acids and a hexitol, for example, polyoxyethylene sorbitol monoleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring phosphatides, for example, soya bean licithin, and esters or partial esters derived from fatty acids and hexitol anhydrides, for example, sorbitan mono-oleate. The emulsions may also contain sweetening and flavoring agents.

Syrups and elixers may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, the active amidinourea may be administered alone or in admixture with other agents having the same or different pharmacological properties.

The anti-parasitic treatment can be administered in combination with antibiotics such as neomycin or with other antibacterial or antiviral agents, or other adjuvants such as eletrolytes and antiemetics. The compounds of Formula I can also be used as a preventive measure, in which case, the preferred mode of administration is through the diet as a feed or water additive.

I claim:

1. A method of treating animals for the suppression of filariasis which comprises administering to an infected animal in need of such treatment an effective amount of an amidinourea of the formula:

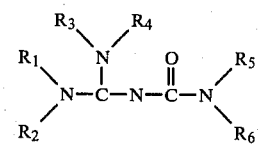

wherein one of $R_1$ or $R_5$ is phenyl, phenyl in which one or more of the hydrogens is substituted by halo, lower alkyl, halo lower alkyl, nitro, amino, acylamino, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ or $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; or a pharmaceutically acceptable salt thereof.

2. A method of treating animals for the suppression of protozoal infestations which comprises administering to an infected animal in need of such treatment an effective amount of an amidinourea of the formula:

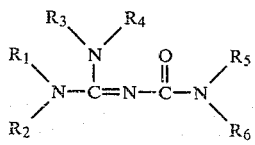

wherein: $R_5$ is substituted phenyl in which both ortho hydrogens are substituted by halo, lower alkyl, halo lower alkyl, nitro, amino, acylamino, lower alkoxy, hydroxy, aryl lower alkoxy, acyloxy, cyano, halo lower alkoxy, or lower alkyl sulfonyl; aralkyl; pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and $R_1$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; or, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, cyclo lower alkyl or aralkyl;

or a pharmaceutically acceptable salt thereof.

3. A method of treating animals for the suppression of protozoal infestations which comprises administering to an infected animal in need of such treatment an effective amount of an amidinourea of the formula:

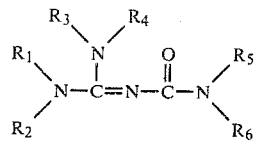

wherein: $R_1$ is substituted phenyl in which both ortho hydrogens are substituted by halo, lower alkyl, helo lower alkyl, nitro, amino, acylamino, lower alkoxy, hydroxy, aryl lower alkoxy, acyloxy, cyano, halo lower alkoxy, or lower alkyl sulfonyl; aralkyl; pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; or, $R_5$ and $R_6$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl;

or a pharmaceutically acceptable salt thereof.

4. A method of treating animals for the suppression of a blood residing parasitic protozoal or filarae infestations which comprises administering to an infected animal in need of such treatment an effective amount of an amidinourea of the formula:

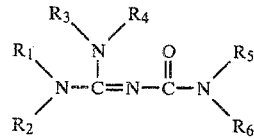

wherein one of $R_1$ or $R_5$ is substituted phenyl in which both ortho hydrogens are substituted by halo, lower alkyl, halo lower alkyl, nitro, amino, acylamino, lower alkoxy, hydroxy, aryl lower alkoxy, acyloxy, cyano, halo lower alkoxy, or lower alkyl sulfonyl; aralkyl; pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ or $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl substituted as above, $R_1$ and $R_2$ together with the nitrogen to which they are attached may be a 5 to 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl;

or a pharmaceutically acceptable salt thereof.

5. A method according to claim 3 wherein the amidinourea or salt which is administered is respectively 1-(2,6-dichlorphenyl amidino)-3-n-propylurea or salt thereof.

6. A method according to claim 1, 2, 3 or 4 wherein the amidinourea or salt is administered with a therapeutically acceptable carrier.

7. A method according to claim 1, 2, 3 or 4 wherein the amidinourea or salt is orally administered to the afflicted animal together with a therapeutically acceptable carrier.

8. A method according to claim 1, 2, 3 or 4 wherein the amidinourea or salt is administered to the afflicted animal as a feed additive.

9. A method according to claim 1, 2, 3 or 4 wherein the amidinourea or salt is administered in a dosage of between about 5 mg/kg body weight to about 15 mg/kg body weight.

10. A method according to claim 1, or 4 wherein the filariasis is canine heartworm.

11. A method according to claim 2 or 3 wherein the protozoal infestation treated is Bovine Anaplasmosis.

12. A method according to claim 2 or 3 wherein the protozoal infestation treated is Texas Fever.

13. A method according to claim 2 or 3 wherein the protozoal infestation treated is Equine Piroplasmosis.

14. A method according to claim 1, 2, 3 or 4 wherein the amidinourea or salt which is administered is in combination with an antibiotic.

15. A method according to claim 2 comprising administering said amidinourea or said salt to an animal infected with a blood residing parasitic protozoal infestation.

16. A method according to claim 3 comprising administering said amidinourea or said salt to an animal infected with a blood residing parasitic protozoal infestation.

17. A method for the suppression of protozoal infestations of animals which comprises administering to an infected animal an effective amount of an amidinourea of the formula:

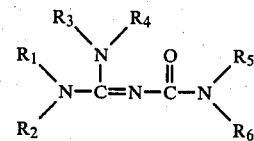

wherein $R_1$ is substituted phenyl in which at least one ortho hydrogen is substituted by halo, lower alkyl, halo lower alkyl, nitro, lower alkoxy, hydroxy, aryl lower alkoxy, acyloxy, cyano, amino, acylamino, halo lower alkoxy, or lower alkyl sulfonyl; aralkyl; pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; or $R_5$ and $R_6$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; or a pharmaceutically acceptable salt thereof.

* * * * *